United States Patent [19]

Uhm et al.

[11] Patent Number: 5,430,178

[45] Date of Patent: Jul. 4, 1995

[54] PROCESS FOR THE PREPARATION OF ACETIC ESTERS FROM METHANOL

[75] Inventors: Sung J. Uhm, Seoul; Sung H. Han, Kyonggi-do; Jun W. Oh, Seoul; Oh S. Joo, Seoul; Kwang D. Jung, Seoul; Moon S. Lee, Seoul, all of Rep. of Korea

[73] Assignee: Korea Institute of Science and Technology, Seoul, Rep. of Korea

[21] Appl. No.: 281,187

[22] Filed: Jul. 27, 1994

[30] Foreign Application Priority Data

Jul. 28, 1993 [KR] Rep. of Korea .............. 93-14392

[51] Int. Cl.$^6$ ............................................. C07C 67/36
[52] U.S. Cl. .................................... 560/232; 560/234
[58] Field of Search ............................... 560/232, 234

[56] References Cited

U.S. PATENT DOCUMENTS

| | | | |
|---|---|---|---|
| 1,864,643 | 6/1932 | Dreyfus et al. | 560/232 |
| 4,246,195 | 1/1981 | Szeisi | 560/232 |
| 4,514,336 | 4/1985 | Ryan | 560/232 |
| 4,664,753 | 5/1987 | Erpenbach et al. | 560/232 |
| 4,690,912 | 9/1987 | Paulik et al. | 560/232 |
| 4,810,821 | 3/1989 | Paulik et al. | 560/232 |
| 5,026,908 | 6/1991 | Smith et al. | 560/232 |
| 5,144,068 | 9/1992 | Smith et al. | 560/232 |
| 5,185,462 | 2/1993 | Evans | 560/232 |
| 5,189,203 | 2/1993 | Hansen | 560/232 |
| 5,214,203 | 5/1993 | Koyoma et al. | 560/232 |

FOREIGN PATENT DOCUMENTS

| | | |
|---|---|---|
| 593337 | 3/1960 | Canada . |
| 131998 | 1/1985 | European Pat. Off. . |
| 353722 | 2/1990 | European Pat. Off. . |
| 0164838 | 8/1981 | Japan . |
| 0199853 | 10/1985 | Japan . |
| 2146637 | 4/1985 | United Kingdom . |

*Primary Examiner*—Paul J. Killos
*Attorney, Agent, or Firm*—Oblon, Spivak, McClelland, Maier & Neustadt

[57] ABSTRACT

Acetic ester is produced economically by a gas phase carbonylation of methanol with carbon monoxide followed by a transesterification. Specifically, the inventive process comprises (a) carbonylating methanol in a gas phase with carbon monoxide to produce a mixture of acetic acid and methyl acetate; (b) separating from the production mixture the acetic acid, and a mixture of the methyl acetate and the co-catalyst; (c) further separating said methyl acetate and the co-catalyst and recycling the separated co-catalyst to the carbonylation reactor; (d) introducing the separated methyl acetate into a lower region of a transesterification reactor at a temperature of above its boiling point; (e) introducing an $C_2$ or higher alcohol into an upper region of the trans-esterification reactor at a temperature of up to its boiling point; (f) transesterifying the methyl acetate with the alcohol in the presence of an acid catalyst to produce a mixture containing acetic esters; and (g) recovering the acetic esters from the mixture as a bottom product while recycling the unreacted methyl acetate and methanol to the carbonylation reactor or distillation column.

12 Claims, 1 Drawing Sheet

PROCESS FOR THE PREPARATION OF ACETIC ESTERS FROM METHANOL

FIELD OF THE INVENTION

The present invention relates to a process for preparing acetic esters from methyl acetate selectively obtained by a gas phase carbonylation of methanol.

BACKGROUND OF THE INVENTION

Acetic esters including alkyl acetate have been widely employed as solvents and plasticizers. Specifically, ethyl acetate, propyl acetate, butyl acetate, isobutyl acetate, isoamyl acetate and the like with a low molecular weight are frequently used as a solvent for lacquers, paints, warnishes, adhesives, etc.; and such acetates as dioctyl phthalate, dibutyl phthalate, and butyl oleate of a high molecular weight are largely used as a plasticizer.

Acetic esters have generally been prepared by an esterification of acetic acid with an alcohol. However, in such esterification, in order to increase the conversion rate, the desired ester product should be removed from the reaction system as the esterification proceeds because the esterification is reversible.

Method of recovering the desired ester varies, depending on a number of factors; such as the difference in the boiling point of the alcohol and the resulting ester, the formation of an azeotrope between the alcohol and water, which is produced during the esterification, or between the ester and water, and so forth. When the boiling point of the resulting ester is lower than that of the corresponding alcohol, it may be readily removed from the reaction product. However, when the boiling point of the resulting ester is equal to or higher than that of the alcohol, its removal process may become rather complex.

For example, ethyl acetate forms a two-component azeotrope with water, and a three-component azeotrope with ethanol and water (ethyl acetate:ethanol:water=83%: 9%: 8%). Processes for producing ethyl acetate using such properties in a batch or continuous system are disclosed in U.S. Pat. Nos. 1,425,624; 1,425,625; 1,454,462 and 1,454,463 assigned to U.S. Industrial Alcohol Co.

Recently, a reactive distillation process has been developed as an improved process, which comprises introducing a high boiling acidic liquid catalyst at the top of the distillation column, and distilling the resulting reaction mixture while carrying out the reaction on each tray of the column. This process, however, has to deal with the problems associated with the catalyst recovery and the reactor corrosion.

SUMMARY OF THE INVENTION

It is, therefore, a primary object of the invention to provide an efficient and economical process for the production of an acetic ester by way of a gas phase carbonylation of methanol to selectively produce methyl acetate followed by the transesterification thereof.

In accordance with the present invention, there is provided a process for producing economically an acetic ester, which comprises:

(a) carbonylating methanol in a gas phase with carbon monoxide in a carbonylation reactor, said carbon monoxide being optionally in admixture of hydrogen, in the presence of a rhodium catalyst comprised of a rhodium compound and a second catalyst component selected from the group consisting of an alkali metal, an alkaline earth metal, a transition metal, a non-metal, and a mixture thereof, and supported on an inert material, and a halide co-catalyst under mild carbonylation conditions and a high GHSV (Gas Hourly Space Velocity) of methanol to produce a mixture of acetic acid and methyl acetate;

(b) separating from the mixture in a distillation column the acetic acid as a high boiling fraction thereof, and a mixture of the methyl acetate and the co-catalyst as a low boiling fraction thereof;

(c) separating the co-catalyst from the low boiling fraction and recycling it to the carbonylation reactor;

(d) introducing the separated methyl acetate from the low boiling fraction into a lower region of a transesterification reactor at a temperature of above its boiling point;

(e) introducing a $C_2$ or higher alcohol into an upper region of the transesterification reactor at a temperature of up to its boiling point;

(f) transesterifying the methyl acetate with the alcohol in the presence of an acid catalyst to produce a mixture containing the desired acetic ester; and (g) recovering the acetic ester from the mixture as a bottoms product while recycling the unreacted methyl acetate and methanol to the carbonylation reactor.

DETAILED DESCRIPTION OF THE INVENTION

Figure 1:
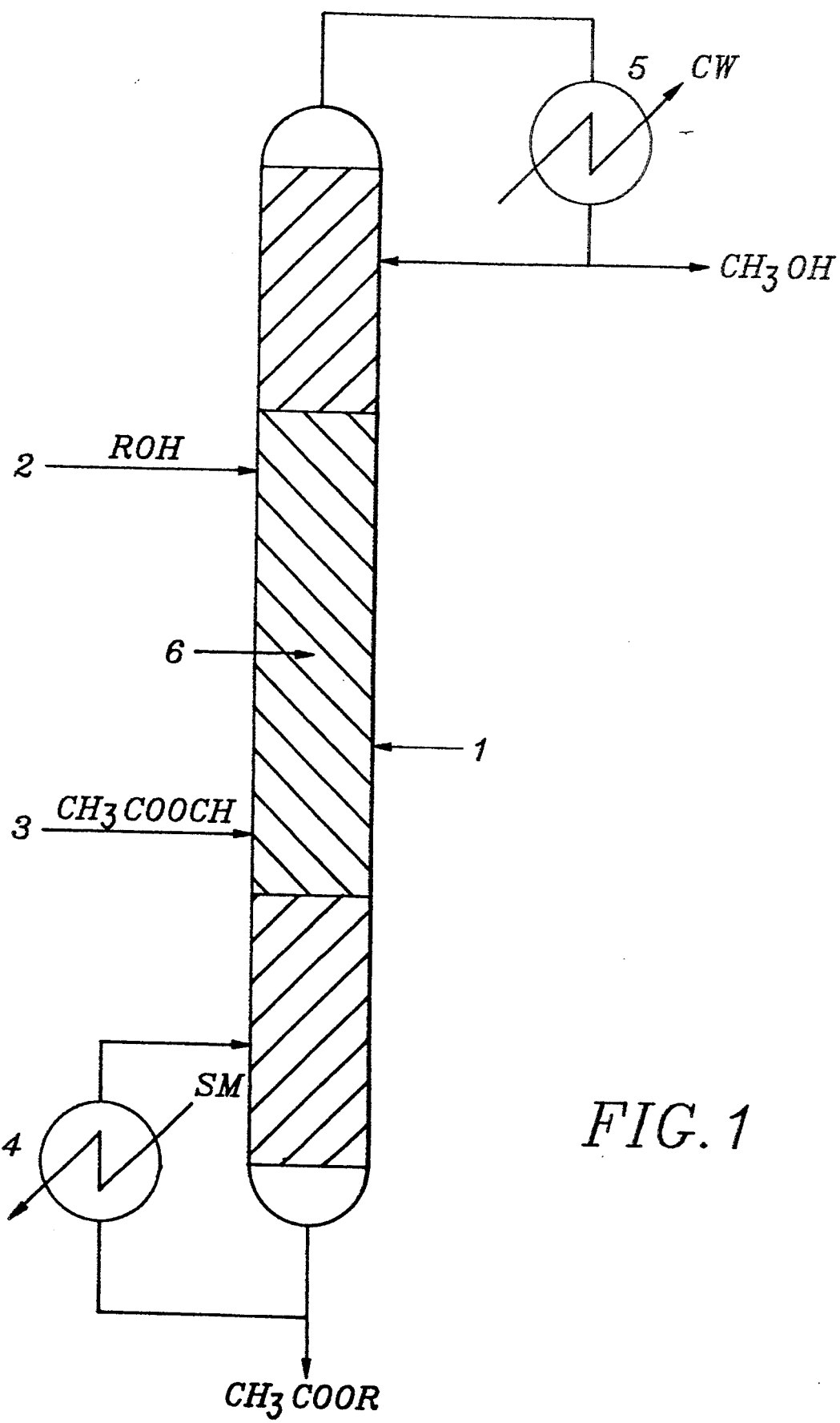
FIG. 1 is a schematic plan showing a catalytic distillating device for carting out transesterification.

In accordance with the present invention, acetic esters are economically produced by conducting a gas phase carbonylation of methanol with carbon monoxide in the presence of a rhodium catalyst and a halide co-catalyst (which is sometimes called a promoter), said carbon monoxide being optionally in admixture of hydrogen gas, under a controlled reaction condition to produce a mixture of a major amount of methyl acetate and a minor amount of acetic acid and then trans-esterifying the methyl acetate with a $C_2$ or higher alcohol to convert it to the desired end product, i.e., a $C_2$ or higher alkyl acetate, at a high yield without the reactor corrosion problem.

A. Production of Methyl Acetate

During the gas phase carbonylation process, selectivity to the desired methyl acetate can be increased in a simple manner in accordance with the present invention. That is, the carbonylation is carried out at a shorter contact time of the reactants with the catalyst as inversely represented by a higher GHSV of methanol ranging from 1 to 100,000 $hr^{-1}$, more preferably from 500 to 50,000 $hr^{-1}$, and most preferably from 1,000 to 10,000 $hr^{-1}$; and at milder reaction conditions: i.e., a lower pressure ranging from 1 to 300 atm, more preferably from 5 to 25 atm, and most preferably from 8 to 15 atm, and a lower reaction temperature ranging from room temperature to 500° C., more preferably from 100° to 300° C. and most preferably from 150° to 270° C. to obtain methyl acetate at a higher yield.

Carbon monoxide(CO) gas is preferably pretreated by contacting the CO gas with a halogen to remove impurities, e.g., metallic carbonyl compounds, contained therein which tend to contaminate or poison the rhodium catalyst employed in the carbonylation process rather rapidly, rendering the process commercially ineffective.

Specifically, the CO gas is fed into a purification column wherein a halogen, for example, iodine, is introduced. The amount of iodine to be used is determined as a function of the flow rate of the feed gas and the column temperature. Said iodine is introduced into the column in a molar amount ranging from 0.1 to 1,000, more preferably from 0.5 to 100, and, most preferably, from 1 to 10 times the metallic content in the feed gas. Several trays may be installed in the column to ensure good mixing between the feed gas and the iodine. The purification column is preferably maintained at a temperature in a range from 150° C. to 200° C., to allow the metallic carbonyl impurities contained in the feed gas to react completely with the halogen gas. The metallic halides so formed, e.g., iron and/or nikel iodide, are sent to an adsorption column and adsorbed onto the adsorbent therein, producing the desired purified feed gas. Examples of the adsorbent which may be used in the purification process include activated carbon, clay, alumina, silica, silica-alumina, zeolite and other adsorbents commonly used in the art. The feed gas thus purified is transferred to the carbonylation reactor wherein said methyl acetate is produced.

Further, an appropriate amount of hydrogen (e.g., about 10 mol % based on the carbon monoxide used) can be beneficially injected into the feed stream of carbon monoxide so as to further enhance the conversion rate of methanol.

After the pretreatment discussed above, the carbon monoxide may be introduced to the carbonylation reactor at a pressure near or slightly higher than the reaction pressure, e.g., 13 atm, and at a temperature preheated to a desired reaction temperature, e.g., 250° C.; and employed in a molar ratio of methanol to carbon monoxide ranging from 1:0.1 to 1:100, more preferably 1:0.5 to 1:50, and most preferably 1:0.8 to 1:3.

Similarly, methanol is preferably preheated and vaporized to the desired reaction temperature and pressure prior to its introduction into the reaction system.

As an exemplary embodiment, carbonylation of methanol loaded on a support with carbon monoxide can be carried out by using $RhCl_3+CuCl_2$ as the catalyst and $CH_3I$ as the co-catalyst at the reaction temperature of 233° C. and the reaction pressure of 150 psi. Said methanol is passed through the catalyst beds at a GHSV of 5995 $hr^{-1}$ to produce 88.4 mol % of methyl acetate and 11.6 mol % of acetic acid. The production mixture together with the methyl iodide is then sent to a distillation column to separate: said acetic acid and water, if any, as the bottoms product; essentially the entire amount of the methyl iodide and an azeotropic amount of the methyl acetate as the light end product of the distillation column (wherein the azeotropic composition of $CH_3I:CH_3COOCH_3$ is 94.2 mol %:5.8 mol % at the azeotropic boiling temperature of 42.1° C.), which are recycled to the carbonylation reactor; and the remaining major portion of the methyl acetate for recovery as an intermediate fraction of the distillation column. The methyl acetate so recovered is essentially dry, which is suitable for use in producing acetic esters in accordance with the present invention.

The rhodium catalyst for use in carrying out the gas phase carbonylation of methanol in accordance with the present invention comprises a rhodium compound and a second catalyst component selected from the group consisting of an alkali metal, an alkaline earth metal, a transition metal, a non-metal, and a mixture thereof; and may be prepared by depositing the rhodium compound dissolved in water or an organic solvent, e.g., an alcohol, on an inert supporting material together with the second component and calcining the resultant at a temperature ranging from 200° to 500° C. The inert supporting material which may be used in preparing the catalyst includes active carbon, clay, alumina, silica, silica-alumina, alumina-phosphate, alumina-silica-phosphate, magnesia, zirconia and the like.

Any of the rhodium compounds, which are soluble in water or an organic solvent and can be calcined at the temperature range of 200° to 500° C., may be used. Representative of such rhodium compounds are: $RhX_3$, $RhX_3 \cdot 3H_2O$, $Rh_2(CO)_4X_2$, $[Rh(CO)X_4]Y$, $Rh_2(CO)_8$, $Rh(NO_3)_3$, $[Rh(CO)_2X_2]Y$, $Rh_2O_3$, $Rh(CH_3COO)_3$, $[Rh(C_2H_4)_2X]_2$, $Rh[(C_6H_5)_3P]_2(CO)X$, Rh metal, $RhX[(C_6H_5)_3P]_2(CH_3X)_2$, $Rh(SnX_3)[(C_6H_5)P]_3$, $RhX(CO)[(C_6H_5)_3Q]_2$, $(R_4Z)[Rh(CO)_2X]_2$, $(R_4Z)_2[Rh(CO)X_4]$, $RhX[(C_6H_5)_3P]_3$, $RhX[(C_6H_5)_3P]H_2$, $[(C_6H_5)_3P]_3Rh(CO)H$ and $Y_4Rh_2X_2(SnX_3)_4$ wherein X is Cl, Br or I; Y is Na, Li or K; Z is N, As or P; Q is As, P or Sb; and R is a $C_1$ to $C_{12}$ alkyl or aryl group. Preferably, $RhCl_3 \cdot 3H_2O$ or $Rh(NO_3)$ is used.

The rhodium compound may be employed in an amount of 0.01 to 20% by weight, more preferably 0.1 to 10%, most preferably 0.3 to 5% by weight of Rh based on the amount of the supporting material. The transition metal compound may be added in an amount of 1 to 1000 mol %, more preferably 10 to 500 mol %, most preferably 30 to 300 mol %, based on the amount of rhodium. The alkali metal or the alkaline earth metal compound may be added in an amount of 1 to 2,000 mol %, more preferably 50 to 1000 mol %, most preferably 200 to 800 mol %, based on the amount of rhodium.

The alkali metal which may be employed as the second component in the rhodium catalyst includes Li, Na, K, Rb, Cs and Fr.

The alkaline earth metal which may be employed as the second component includes Be, Mg, Ca, Sr, Ba and Ra.

The transition metal which may be employed as the second component includes Co, Ru, Fe, Pd, Pt, Os, Ir, Ni, Mn, Re, Cr, Cu, Ag, Au, Zn, Cd, Hg, Mo, W, V, Nb, Ta, Ti, Zr, Hf, Sc, Y, La and Ac.

The non-metal which may be employed as the component includes Ga, In, Tl, Al, Si, Ge, Sn, Pb, P, As, Sb, Bi, S, Se, Te and Po.

The carbonylation catalyst employed in the present invention is easily prepared by adding at least one of the second metallic compounds such as $CoCl_2$, $RuCl_3$, $PdCl_2$, $PtCl_2$, $CuCl_2$, $AgNO_3$, $AuCl_3$, $CdCl_2$, $ZnCl_2$, $OsCl_3$, $IrCl_3$, $NiCl_2$, $MnCl_2$, $ReCl_5$, $CrCl_3$, $MoCl_3$, $WCl_6$, $VCl_3$, $NbCl_5$, $TaCl_5$, $TiCl_4$, $ZrCl_4$, $HfCl_4$, LiI, NaI, KI, RbCl, $BeCl_2$, $MgCl_2$, $CaCl_2$, $SrCl_2$ and $BaCl_2$ in a specified amount to a rhodium compound deposited on the inert material.

The inventive gas phase process for selectively producing methyl acetate is carried out by using a halide co-catalyst in the presence of the rhodium catalyst.

The halide compound which may be employed as the co-catalyst includes: $CH_3I$, $CH_3Br$, $CH_3Cl$, $I_2$, $Br_2$, $Cl_2$, HI, HBr, HCl and the like. Among them, $CH_3I$ is preferred.

The halide co-catalyst may be employed in a molar ratio of the co-catalyt per mole of the methanol used ranging from 0.001 to 5, more preferably from 0.01 to 1 and most preferably from 0.05 to 0.15.

The acid catalyst which may be employed in the present invention is selected from the group consisting of natural clayminerals, $H_2SO_4$, $H_3PO_4$ and $CH_2(COOH)_2$, in the form of being mounted on silica, quartz sand, alumina or diatomaceous earth; cation exchange resins, heat treated charcoals, metal oxides and sulfides, metal salts, mixed oxides and heteropoly acids.

It should be noted that the separated mixture of methanol and methyl acetate is recycled to the carbonylation reactor, thereby to make the overall process more economical.

B. Production of Acetic Ester

Acetic ester, particularly $C_2$ or higher alkyl acetate, is synthesized conveniently from the methyl acetate obtained in accordance with the carbonylation process of the present invention.

As described above, in the carbonylation process, methyl acetate is produced in a high selectivity, e.g., in excess of 88%, by a simple adjustment of the reaction conditions and by using a suitable catalyst, e.g., $RhCl_3+CuCl_2$ on active carbon. From the reaction mixture, methyl acetate and the co-catalyst can easily be separated from the rest of the mixture as a low boiling fraction in a distillation column. Further, the acetic acid can be recovered from the reaction mixture as a high boiling fraction.

All or a major portion of the methyl acetate is subsequently separated from the co-catalyst in a distillation column; and the separated methyl acetate is introduced into a lower region of a transesterification reactor, which is a distillation column adapted for the purpose of the present invention, at a temperature above its boiling point while the separated co-catalyst with or without a minor portion of methyl acetate is recycled to the carbonylation reactor. Further, $C_2$ or higher alcohol is introduced into an upper region of the transesterification reactor at a temperature of up to its boiling point. In the transesterification reactor, methyl acetate is transesterified with the alcohol to produce a reaction mixture containing a $C_2$ or higher alkyl acetate as the reaction products are being separated, within an acid catalyst bed, which is placed at a center portion of the reactor. That is, the resulting alkyl acetate can be obtained as a bottoms product of the reactor and the mixture of methyl acetate and methanol can be obtained as a top product of the reactor, which is preferably recycled to the carbonylation reactor or methylacetate distillation column.

The acid catalyst bed is filled with an acid catalyst, which may be an solid acid, i.e., an ion exchange resin, treated with an acid by using a conventional method.

A preferred embodiment of the transesterification reactor for the purpose of the present invention is shown in FIG. 1. Referring to FIG. 1, a distillation column 1, made of pyrex, has an inner diameter of 15 mm and a height of 150 cm. The injection ports for alcohol and methyl acetate 2 and 3 are placed at a distance of 45 cm from the top and bottom of the column, respectively, and spaced each other at a 60 cm distance. A reboiler 4 in an oil bath are installed at the bottom of the column; and a U-tube filled with distilled water for measuring the pressure drop of the column is placed between the reboiler 4 and the condenser 5.

At the middle portion, i.e., 75 cm from the top or bottom of the column, a catalyst bed 6 filled with an acid catalyst is placed, and the remaining space of the column is filled with helices rings. As an acid catalyst, Amberlyst ® treated with an acid, e.g., $H_2SO_4$, by a conventional method is employed. The helices rings function to separate the reaction mixture into products and unreacted components and then to pass the products to the top and the bottom of the column while passing the unreacted components to the reaction region.

Thermometers are installed at the inside of the column for measuring the internal temperature of the column; and glass wool (not shown) is installed around the outside of the column in a 2 cm thickness for the insulation thereof. Further, at the top of the column, a solenoid valve and a time controller are installed so that the product condensed in the condenser can be constantly refluxed.

Methyl acetate and an alcohol are separately introduced in a constant amount into the lower region and the upper region of the column 1, respectively, by way of a pump and then a preheater. The methyl acetate is maintained at a temperature of equal to or higher than its dew point and the alcohol is maintained at a temperature of equal to or lower than its boiling point. After the trans-esterification is completed, the desired $C_2$ or higher alkyl acetate and the mixture of methyl acetate and methanol can be recovered as a bottoms product and a top product, repectively.

As mentioned previously, in accordance with the present invention, $C_2$ or higher alkyl acetate can be economically synthesized from methyl acetate obtained in a high yield in accordance with the inventive transesterification process.

In accordance with the transesterification of the present invention, a variety of esters can be obtained by replacing the alkyl group or the carboxyl group of the resulting ester with a desired other group.

It is important to note that the essentially dry methyl acetate obtained from the carbonylation process of the present invention is beneficially employed in the transesterification process to thereby obviate the costly drying operation required in the prior art processes of producing methyl acetate from the esterification of acetic acid with methanol.

The following Examples are given for the purpose of illustration only and are not intended to limit the scope of the invention.

EXAMPLE 1

A carbonylation catalyst was prepared as follows: $RhCl_3$ and LiI were supported on active carbon by impregnating the carbon in a solution of $RhCl_3$ and LiI such that 0.6% by weight of Rh based on the amount of the active carbon and 400 mol % of LiI based on the amount of Rh were supported thereon. The resulting material was then calcined at 300° C.

A reactor tube, having an inside diameter of 1.27 cm (0.5 inch) and a length of 40 cm, was charged with 5 g of the catalyst. The reactor tube was filled with glass fiber, pretreated in a NaOH solution, at the top and the bottom ends thereof so as to form a catalyst bed of 10 cm in length therein; and, a thermowell having an outside diameter of 0.64 cm (0.25 inch) with a thermocouple was inserted in the center of the reactor tube.

The reactor tube was oil jacketed so as to heat it with a heating medium. Methanol and carbon monoxide, pretreated with iodine, in a molar ratio of 1:2.3 were introduced into the reactor tube; and were allowed to react in the presence of 10 mol % of the co-catalyst, $CH_3I$, based on the amount of the methanol used, at an inside temperature of about 233° C. under a pressure of 150 psi.

The conversion of methanol, and the yields of acetic acid and methyl acetate obtained, depending on the GHSV of methanol under the above conditions, are shown in Table 1.

TABLE 1

| GHSV (hr$^{-1}$)[1] | 1207 | 1568 | 1735 | 2133 | 3293 | 3652 | 4149 |
|---|---|---|---|---|---|---|---|
| Methanol conversion (%) | 96.4 | 93.7 | 88.9 | 84.3 | 71.6 | 68.8 | 62.2 |
| Yield of[2] acetic acid (%) | 33.0 | 22.3 | 20.0 | 15.5 | 10.7 | 8.6 | 7.5 |
| Yield of[3] methyl acetate (%) | 63.0 | 64.8 | 64.8 | 63.6 | 60.1 | 54.5 | 49.5 |

[1] GHSV = Gas Hourly Space Velocity (hr$^{-1}$) of methanol: This is a measure of determining the amount of the reactant, i.e., gasified methanol, passing through the catalyst beds per hour. The higher the GHSV, the shorter the contact time of the catalyst with the reactant becomes, rendering the amount of the reactant to be treated per hour larger.

[2] Yield of acetic acid = $\frac{\text{Moles of acetic acid produced}}{\text{Moles of methanol introduced}} \times 100$

[3] Yield of methyl acetate = $\frac{\text{Moles of methyl acetate produced} \times 2}{\text{Moles of methanol introduced}} \times 100$

EXAMPLE 2

This Example was carried out in the same manner as described in Example 1, except that a catalyst supported on active carbon and containing 0.6% by weight of Rh based on the amount of the active carbon and 50 mol % $CuCl_2$ based on the amount of Rh, together with the different values of GHSV, was employed. The results are shown in Table 2.

TABLE 2

| GHSV(hr$^{-1}$) | 1979 | 3596 | 4856 | 5995 |
|---|---|---|---|---|
| Methanol conversion (%) | 98.2 | 95.8 | 87.0 | 78.7 |
| Yield of acetic acid (%) | 45.4 | 26.7 | 15.4 | 8.9 |
| Yield of methyl acetate (%) | 52.8 | 68.0 | 71.2 | 67.8 |

EXAMPLE 3

This Example was carried out as described in Example 1, except that a catalyst supported on active carbon and containing 0.6% by weight of Rh based on the amount of the active carbon and 200 mol % of NaI based on the amount of Rh was employed, and the reaction temperature and the pressure were changed to 240° C. and 200 psi, respectively, in addition to the different values of GHSV. The results are shown in Table 3.

TABLE 3

| GHSV(hr$^{-1}$) | 1000 | 1568 | 1735 | 2133 |
|---|---|---|---|---|
| Methanol conversion (%) | 100 | 99.9 | 100 | 99.7 |
| Yield of acetic acid (%) | 82.0 | 57.4 | 38.8 | 31.1 |

TABLE 3-continued

| GHSV(hr$^{-1}$) | 1000 | 1568 | 1735 | 2133 |
|---|---|---|---|---|
| Yield of methyl acetate (%) | 17.1 | 42.1 | 60.0 | 67.9 |

EXAMPLE 4

This Example was carried out in the same manner as described in Example 1, except that a catalyst supported on active carbon and containing 0.6% by weight of Rh based on the amount of the active carbon and 200 mol % of KI based on the amount of Rh, together with the different values of GHSV, was employed. The results are shown in Table 4.

TABLE 4

| GHSV(hr$^{-1}$) | 1039 | 1795 | 2997 | 4017 |
|---|---|---|---|---|
| Methanol conversion (%) | 100 | 100 | 99.7 | 96 |
| Yield of acetic acid (%) | 94.8 | 80.0 | 50.1 | 30.1 |
| Yield of methyl acetate (%) | 5.1 | 19.9 | 48.9 | 60.5 |

EXAMPLE 5

This Example was carried out as described in Example 1, except that a catalyst supported on active carbon and containing 0.6% by weight of Rh based on the active carbon and 50 mol % of $MgCl_2$ based on the Rh, together with the different values of GHSV, was employed. The results are shown in Table 5.

TABLE 5

| GHSV(hr$^{-1}$) | 2068 | 3417 | 4855 | 5754 |
|---|---|---|---|---|
| Methanol conversion (%) | 100 | 98.8 | 94.6 | 84.9 |
| Yield of acetic acid (%) | 89.9 | 66.6 | 43.1 | 30.0 |
| Yield of methyl acetate (%) | 8.8 | 30.6 | 49.6 | 52.3 |

EXAMPLE 6

This Example was carried out as described in Example 1, except that a catalyst supported on active carbon and containing 0.6% by weight of Rh based on the active carbon and 50 mol % of $IrCl_3$ based on the Rh was employed, and the reaction temperature was changed to 255° C., in addition to the different values of GHSV. The results are shown in Table 6.

TABLE 6

| GHSV(hr$^{-1}$) | 800 | 1200 | 1500 | 2000 | 2500 |
|---|---|---|---|---|---|
| Methanol conversion (%) | 99.0 | 100 | 99.7 | 99.9 | 99.8 |
| Yield of acetic acid (%) | 74.0 | 53.8 | 38.9 | 27.7 | 18.3 |
| Yield of methyl | 24.1 | 44.3 | 60.1 | 71.0 | 80.1 |

TABLE 6-continued

| GHSV(hr$^{-1}$) | 800 | 1200 | 1500 | 2000 | 2500 |
|---|---|---|---|---|---|
| acetate (%) | | | | | |

EXAMPLE 7

This Example was carried out as described in Example 1, except that a catalyst supported on active carbon and containing 0.6% by weight of Rh based on the active carbon and 200 mol % of PdCl$_2$ based on the Rh was employed; and the reaction temperature and the pressure were changed to 255° C. and 150 psi, respectively, in addition to the different values of GHSV. The results are shown in Table 7.

TABLE 7

| GHSV(hr$^{-1}$) | 1000 | 2000 | 3000 | 4000 |
|---|---|---|---|---|
| Methanol conversion (%) | 99.1 | 95.2 | 85.3 | 78.1 |
| Yield of acetic acid (%) | 54.5 | 28.5 | 16.1 | 13.2 |
| Yield of methyl acetate (%) | 43.5 | 65.5 | 67.8 | 63.7 |

EXAMPLE 8

This Example was carried out as described in Example 1, except that a catalyst supported on active carbon and containing 0.6% by weight of Rh based on the active carbon and 50 mol % of RuCl$_3$ based on the Rh was employed, and the reaction temperature was changed to 255° C., in addition to the different values of GHSV. The results are shown in Table 8.

TABLE 8

| GHSV(hr$^{-1}$) | 1800 | 3000 | 4200 |
|---|---|---|---|
| Methanol conversion (%) | 93 | 84 | 73 |
| Yield of acetic acid (%) | 22.3 | 10.9 | 0.8 |
| Yield of methyl acetate (%) | 68.8 | 71.4 | 61.8 |

EXAMPLE 9

This Example was carried out as described in Example 1, except that a catalyst supported on active carbon and containing 0.6% by weight of Rh based on the active carbon and 50 mol % of CoCl$_2$ based on the Rh was employed; and the reaction temperature was changed to 210° C., in addition to the changed values of GHSV. The results are shown in Table 9.

TABLE 9

| GHSV(hr$^{-1}$) | 1000 | 2000 | 3000 | 4000 |
|---|---|---|---|---|
| Methanol conversion (%) | 99.9 | 98.0 | 91.1 | 82.3 |
| Yield of acetic acid (%) | 45.0 | 32.3 | 19.9 | 12.3 |
| Yield of methyl acetate (%) | 53.8 | 64.6 | 70.1 | 68.9 |

TABLE 9-continued

| GHSV(hr$^{-1}$) | 1000 | 2000 | 3000 | 4000 |
|---|---|---|---|---|
| acetate (%) | | | | |

EXAMPLE 10

This Example was carried out as described in Example 1, except that a catalyst supported on active carbon and containing 0.6% by wieght of Rh based on the active carbon and 50 mol % of NiCl$_2$ based on the Rh was employed, and the reaction temperature was changed to 210° C., in addition to the different values of GHSV. The results are shown in Table 10.

TABLE 10

| GHSV(hr$^{-1}$) | 1000 | 2000 | 3000 | 4000 |
|---|---|---|---|---|
| Methanol conversion (%) | 100 | 95.0 | 90.2 | 79.3 |
| Selectivity to acetic acid (%) | 49.9 | 39.1 | 29.1 | 18.0 |
| Selectivity to methyl acetate (%) | 50.1 | 59.9 | 70.1 | 81.3 |

EXAMPLE 11

This Example was carried out as described in Example 1, except that a catalyst supported on active carbon and containing 0.6% by weight of Rh based on the active carbon and 50 mol % of Mn based on the Rh was employed, and the reaction temperature was changed to 270° C., in addition to the different values of GHSV. The results are shown in Table 11.

TABLE 11

| GHSV(hr$^{-1}$) | 1918 | 3417 | 4722 | 5754 |
|---|---|---|---|---|
| Methanol conversion (%) | 100 | 99.8 | 95.8 | 90.7 |
| Yield of acetic acid (%) | 82.6 | 56.8 | 39.9 | 28.1 |
| Yield of methyl acetate (%) | 16.9 | 34.4 | 51.0 | 59.3 |

EXAMPLE 12

This Example was carried out as described in Example 1, except that a catalyst supported on active carbon and containing 0.6% by weight of Rh based on the active carbon and 25 mol % of Mn and 100 mol % of Li based on the Rh was employed, and the reaction temperature was changed to 270° C., in addition to the changed values of GHSV. The results are shown in Table 12.

TABLE 12

| GHSV(hr$^{-1}$) | 2278 | 3476 | 4856 | 6235 |
|---|---|---|---|---|
| Methanol conversion (%) | 100 | 100 | 96.9 | 88.5 |
| Yield of acetic acid (%) | 87.7 | 71.7 | 53.9 | 35.8 |
| Yield of methyl acetate (%) | 4.7 | 17.7 | 31.5 | 38.1 |

EXAMPLE 13

This Example was carried out as described in Example 1, except that a catalyst supported on active carbon and containing 0.6% by weight of Rh based on the active carbon and 50 mol % of Os based on the Rh was employed, and the reaction temperature was changed to 270° C., with the different values of GHSV. The results are shown in Table 13.

TABLE 13

| GHSV(hr$^{-1}$) | 2278 | 3596 | 4856 | 6115 |
|---|---|---|---|---|
| Methanol conversion (%) | 99.1 | 97.7 | 93.0 | 85.3 |
| Yield of acetic acid (%) | 58.7 | 37.0 | 22.7 | 16.8 |
| Yield of methyl acetate (%) | 30.2 | 52.4 | 61.8 | 62.7 |

EXAMPLE 14

Ethyl acetate was prepared in accordance with the following procedure.

Into a distillation column as shown in FIG. 1 as a transesterification reactor was supplied ethanol at a flow rate of 0.46 mole/hr and at a temperature of 60° C. at an upper region thereof, while supplying methyl acetate obtained in Example 1 above at a flow rate of 1.78 mole/hr and at a temperature of 62° C. to a lower region of the column. Reflux ratio of these components was 3. The temperatures of the reboiler and the top of the reactor were 76.5° C. and 55° C., respectively. The flow rates at the top portion and the bottom portion of the reactor were 1.85 mole/hr and 0.39 mole/hr, respectively. At this time, the conversion was about 80.7%. The concentrations of the products obtained at the top and the bottom portions are shown in Table 14.

TABLE 14

| | Yield of methanol (mole %) | Yield of ethanol (mole %) | Yield of methyl acetate (mole %) | Yield of ethyl acetate (mole %) |
|---|---|---|---|---|
| Concentration at the top portion | 19.88 | 3.13 | 74.67 | 2.32 |
| Concentration at the bottom portion | 0.45 | 7.53 | 7.92 | 83.91 |

EXAMPLE 15

This Example was carried out as described in Example 14, except that the temperature of the reboiler was changed to 79.2° C. and the flow rates at the top and bottom portions of the column were 1.94 mole/hr and 0.29 mole/hr, respectively At this time, the conversion was about 80.4%. The concentrations of the products obtained at the top and the bottom portions are shown in Table 15.

TABLE 15

| | Yield of methanol (mole %) | Yield of ethanol (mole %) | Yield of methyl acetate (mole %) | Yield of ethyl acetate (mole %) |
|---|---|---|---|---|
| Concentration at the top portion | 18.82 | 4.15 | 72.40 | 4.62 |
| Concentration at the bottom portion | 0.45 | 2.43 | 2.39 | 94.72 |

EXAMPLE 16

Butyl acetate was prepared in accordance with the same procedures as described in Example 14, except that butanol was supplied into the column at a flow rate of 0.23 mole/hr and at a temperature of 43.8° C., while supplying methyl acetate obtained in Example 1 above at a flow rate of 0.68 mole/hr and at a temperature of 70.6° C., the reflux ratio of these components was 5, the temperatures of the reboiler and the top portion of the column were 128.7° C. and 53.3° C., respectively, and the flow rates at the top and the bottom portions of the reactor were 0.68 mole/hr 0.23 mole/hr, respectively. The concentrations of the products obtained at the top and the bottom portions are shown in Table 16.

TABLE 16

| | Yield of methanol (mole %) | Yield of ethanol (mole %) | Yield of methyl acetate (mole %) | Yield of ethyl acetate (mole %) |
|---|---|---|---|---|
| Concentration at the top portion | 34.43 | 0.08 | 65.49 | 0.00 |
| Concentration at the bottom portion | 0.00 | 0.00 | 0.00 | 100.00 |

EXAMPLE 17

Isopropyl acetate was prepared in accordance with the same procedures as described in Example 14, except that isopropanol was supplied into the column at a flow rate of 0.26 mole/hr and a temperature of 45.0° C., while supplying methyl acetate obtained in Example 1 above at a flow rate of 0.83 mole/hr and at a temperature of 72.0° C. , the reflux ratio of these components was 5, the temperatures of the reboiler and the top portion of the reactor were 88.0° C. and 54.0° C., respectively, and the flow rates at the top and the bottom portions of the reactor were 0.83 mole/hr 0.26 mole/hr, respectively. The concentrations of the products obtained at the top and the bottom portions are shown in Table 17.

TABLE 17

| | Yield of methanol (mole %) | Yield of ethanol (mole %) | Yield of methyl acetate (mole %) | Yield of ethyl acetate (mole %) |
|---|---|---|---|---|
| Concentration at the top | 30.9 | 69.1 | 0.00 | 0.00 |
| Concentration at the bottom portion | 0.00 | 0.00 | 2.00 | 97.2 |

As can be seen from the above, in accordance with the present invention, $C_2$ or higher alkyl actate can be produced economically by transesterifying the methyl acetate obtained from the selective gas phase carbonylation of methanol with a $C_2$ or higher alcohol.

While the invention has been described respect to the above specific embodiments, it should be recognized that various modifications and changes may be made by those skilled in the art to the invention which also fall within the scope of the invention as defined by the appended claims.

What is claimed is:

1. A process for producing a $C_2$ or higher acetic ester, which comprises:
   (a) carbonylating methanol in a gas phase with carbon monoxide in a carbonylation reactor, said carbon monoxide being optionally in admixture of hydrogen, in the presence of a rhodium catalyst comprised of a rhodium compound and a second catalyst component selected from the group consisting of an alkali metal, an alkaline earth metal, a transition metal, a non-metal, and a mixture thereof, and supported on an inert material, and a halide co-catalyst under mild carbonylation conditions and a high GHSV (Gas Hourly Space Velocity) of methanol to produce a mixture of acetic acid and methyl acetate;

(b) separating from the mixture in a distillation column said acetic acid as a high boiling fraction thereof, and a mixture of said methyl acetate and the co-catalyst as a low boiling fraction thereof;

(c) further separating all or a major portion of said methyl acetate from the co-catalyst in the low boiling fraction and recycling the separated co-catalyst with or without a minor portion of said methyl acetate to the carbonylation reactor;

(d) introducing the separated methyl acetate from the low boiling fraction into a lower region of a transesterification reactor at a temperature above its boiling point;

(e) introducing a $C_2$ or higher alcohol into an upper region of the transesterification reactor at a temperature of up to its boiling point;

(f) transesterifying the methyl acetate with the alcohol in the presence of an acid catalyst to produce a mixture containing the desired alkyl acetate; and (g) recovering the alkyl acetate from the mixture as a bottoms product while recycling the unreacted methyl acetate and methanol to the carbonylation reactor or distillation column.

2. The process of claim 1, wherein said carbon monoxide employed in said step (a) is passed through an adsorption column provided with an adsorbent prior to its introduction into the carbonylation reactor.

3. The process of claim 2, wherein said carbon monoxide is treated with a halogen prior to its passing through the adsorption column.

4. The process of claim 1, wherein said rhodium compound employed in said step (a) is selected from the group consisting of $RhX_3$, $RhX_3 \cdot 3H_2O$, $Rh_2(CO)_4X_2$, $[Rh(CO)X_4]Y$, $Rh_2(CO)_8$, $Rh(NO_3)_3$, $[Rh(CO)_2X_2]Y$, $Rh_2O_3$, $Rh(CH_3COO)_3$, $[Rh(C_2H_4)_2X]_2$, $Rh[(C_6H_5)_3P]_2(CO)X$, Rh metal, $RhX[(C_6H_5)_3P]_2(CH_3X)_2$, $Rh(SnX_3)[(C_6H_5)P]_3$, $RhX(CO)[(C_6H_5)_3Q]_2$, $(R_4Z)[Rh(CO)_2X]_2$, $(R_4Z)_2[Rh(CO)X_4]$, $RhX[(C_6H_5)_3P]_3$, $RhX[(C_6H_5)_3P]H_2$, $[(C_6H_5)_3P]_3Rh(CO)H$ and $Y_4Rh_2X_2(SnX_3)_4$ wherein X is Cl, Br or I; Y is Na, Li or K; Z is N, As or P; Q is As, P or Sb; and R is a $C_1$ to $C_{12}$ alkyl or aryl group.

5. The process of claim 1, wherein said alkali metal is selected from the group consisting of Li, Na, K, Rb, Cs and Fr.

6. The process of claim 1, wherein said alkaline earth metal is selected from the group consisting of Be, Mg, Ca, Sr, Ba and Ra.

7. The process of claim 1, wherein said transition metal is selected from the group consisting of Cu, Ag, Au, Zn, Cd, Co, Ru, Pd, Pt, Os, It, Ni, Mn, Re, Cr, Mo, W, V, Nb, Ta, Ti, Zr and Hf.

8. The process of claim 1, wherein said non-metal is selected from the group consisting of Ga, In, Tl, Al, Si, Ge, Sn, Pb, P, As, Sb, Bi, S, Se, Te and Po.

9. The process of claim 1, wherein said co-catalyst is selected from the group consisting of $CH_3I$, $CH_3Br$, $CH_3Cl$, $I_2$, $Br_2$, $Cl_2$, HI, HBr and HCl.

10. The process of claim 9, wherein said co-catalyst is $CH_3I$.

11. The process of claim 1, wherein said acid catalyst is selected from the group consisting of natural clayminerals, $H_2SO_4$, $H_3PO_4$ and $CH_2(COOH)_2$, in the form of being mounted on silica, quartz sand, alumina or diatomaceous earth; cation exchange resins, heat treated charcoals, metal oxides and sulfides, metal salts, mixed oxides and heteropoly acids.

12. The process of claim 11, wherein the acid catalyst is a cation-exchange resin.

* * * * *